United States Patent [19]

Takano et al.

[11] Patent Number: 5,129,878
[45] Date of Patent: Jul. 14, 1992

[54] AUXILIARY CIRCULATION APPARATUS AND METHOD OF ITS DRIVING

[75] Inventors: Hisateru Takano; Yoshiyuki Taenaka; Takeshi Nakatani; Eisaku Sasaki, all of Suita; Koichi Hashimoto; Minoru Ikeda, both of Ohtsu, all of Japan

[73] Assignee: Toyo Boseki Kabushiki Kaisha, Osaka, Japan

[21] Appl. No.: 585,878

[22] Filed: Sep. 20, 1990

[30] Foreign Application Priority Data

Sep. 28, 1989 [JP] Japan .................. 1-253115

[51] Int. Cl.⁵ .................................... A61M 1/00
[52] U.S. Cl. ............................................ 600/18
[58] Field of Search .................... 600/16, 17, 18

[56] References Cited

U.S. PATENT DOCUMENTS

| 4,016,871 | 4/1977 | Schiff | 600/18 |
| 4,162,543 | 7/1979 | Shumakov et al. | 600/16 |
| 4,666,443 | 5/1987 | Portner | 600/16 |
| 4,787,368 | 11/1988 | Kageyama | 600/18 |
| 4,796,606 | 1/1989 | Mushika | 600/18 |

Primary Examiner—William E. Kamm
Attorney, Agent, or Firm—Leydig, Voit & Mayer

[57] ABSTRACT

The present invention discloses an assist circulation apparatus and a method of its driving. Use of the apparatus of the present invention and method of its driving permits weaning from the driving or wearing of the ventricular assist device with simple operation without extreme reduction in the output per beat of the ventricular assist device being attached or severely influencing the patient's body upon recovery of the failed heart.

8 Claims, 4 Drawing Sheets

1: ventricular assist device drive console
2: ventricular assist device
3: balloon drive console
4: intra-aortic balloon catheter
5: communication cable
6: ventricular assist device drive element
7: microprocessor
8: balloon drive element
9: microprocessor
10: interlock switch
11: select switch 1: ventricular assist device drive console
2: ventricular assist device
3: balloon drive console
4: intra-aortic balloon catheter
5: communication cable
6: ventricular assist device drive element
7: microprocessor
8: balloon drive element
9: microprocessor
10: interlock switch
11: select switch (a)

(b)

(c)

(x)

AUXILIARY CIRCULATION APPARATUS AND METHOD OF ITS DRIVING

FIELD OF THE INVENTION

The present invention relates to an assist circulation apparatus that facilitates weaning from a ventricular assist device when the failed heart of the patient has almost gained recovery with the aid of the ventricular assist device, and a method of its driving.

BACKGROUND OF THE INVENTION

In recent years, ventricular assist device has been used in cases where it is impossible to well maintain systemic circulation due to deterioration in the pumping function of the subject's heart after cardiovascular surgery, on acute myocardial infarction, etc. In such cases, left heart failure is often dominant, and a ventricular assist device is normally placed in parallel to the left heart of the patient, which serves to supplement the pumping function of the failed heart for a given time and facilitates the functional recovery of the failed heart while maintaining systemic circulation. The bypass flow from the ventricular assist device is decreased according to the degree of functional recovery of the failed heart so that systemic circulation remains constant. Since the ventricular assist device involves the possibility of thrombos formation due to too low a blood flow rate in cases where the bypass flow decreases below a certain level, an intra-aortic balloon catheter (hereinafter referred to as balloon) is normally sued after weaning. When the bypass flow from the ventricular assist device has decreased below a given level, the ventricular assist device is removed and assist circulation is maintained using the balloon alone. Also known is the method in which the ventricular assist device drive console and the balloon drive console are electrocardiographically synchronized to be 1 cycle each per 2 beats of the failed heart (patient's heart) so that the ventricular assist device and the balloon are alternatively driven at a rate of 1 cycle per beat of the failed heart.

When using a ventricular assist device and a balloon in combination, simultaneous occurrence of ventricular assist device systole and balloon inflation causes abnormal increase in aortic pressure, which suppresses output flow from the ventricular assist device and poses a circulation management problem. Already proposed methods include the method in which he diastole is divided into two periods, allotted to the ventricular assist device and the balloon, respectively, and driving timing is adjusted so that ventricular assist device systole and balloon inflation do not occur simultaneously. However, this method is subject to significant limitation on driving conditions and is unsuitable for weaning, since dividing the diastole requires quick driving of the ventricular assist device and balloon. In the above-mentioned method in which the ventricular assist device drive and the balloon drive are electrocardiographically synchronized so that the ventricular assist device and the balloon are alternatively driven at a rate of 1 cycle per beat of the patient's heart. It is necessary to constantly monitor and adjust the operation to ensure alternative driving, since the ventricular assist device and the balloon are sometimes driven simultaneously because their controllers act separately due to electrocardiographic disturbance. In addition, for successful weaning from the ventricular assist device, it is desirable that the balloon driving frequency per beat of the ventricular assist device be increased gradually to reach a given ratio of balloon driving, and then the synchronous ratio of the ventricular assist device to the natural heart be decreased to be removed; however, this is difficult to achieve with conventional assist circulation apparatuses.

SUMMARY OF THE INVENTION

The object of the present invention is to provide an assist circulation apparatus that facilitates smooth weaning from the ventricular assist device while using the balloon without unfavorable influence on the patient's body upon recovery thereof, and a method of its driving.

DETAILED DESCRIPTION OF THE INVENTION

The present invention comprises an assist circulation apparatus that permits the use of a ventricular assist device and an intra-aortic balloon catheter in combination, characterized by a mechanism that allows arbitrary alteration of the ratio of the driving frequencies of these two devices, and a method of driving said assist circulation apparatus, characterized by arbitrary alteration of the ratio of the driving frequencies of the ventricular assist device and the intra-aortic balloon catheter.

With a mechanism equipped with a communication means that allows either the ventricular assist device drive controller or the balloon drive controller to regulate the driving timing of the counterpart, the assist circulation apparatus of the present invention controls the driving of both the ventricular assist device and the balloon to prevent simultaneous driving thereof and alters the ratio of the driving frequencies thereof to increase the balloon driving frequency so that weaning from the ventricular assist device is facilitated without unfavorable influence on the patient's body and driving control becomes easier.

The present invention is hereinafter described in more detail by means of the following example, but the invention is not by any means limited thereto, and specifically, the ventricular assist device drive console and the balloon drive console may be unified.

Figure 1:
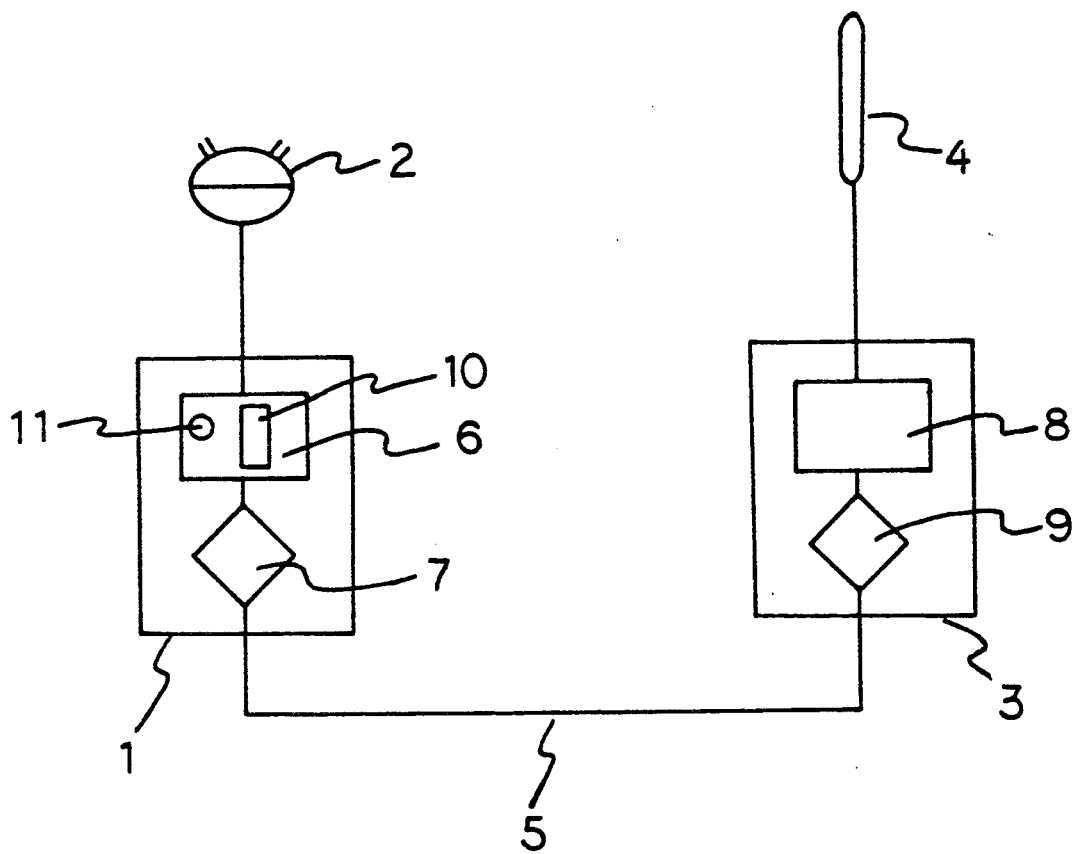
FIG. 1 is an overall schematic of a mode of embodiment of the assist circulation apparatus of the present invention.

A mode of embodiment of the present invention is hereinafter described by means of drawings. FIG. 1 shows an example mode of the assist circulation apparatus of the present invention, i.e., a weaning system for the ventricular assist device. It is configured with a pulsation type ventricular assist device 2, its drive console 1, a balloon 4 and its drive console 3. Drive consoles 1 and 3 are equipped with drive elements 6 and 8, respectively, each comprising a positive pressure source, a negative pressure source, various valves, etc., and also equipped with microprocessors 7 and 9, respectively, and the two drives are interconnected via a communication cable 5.

In addition, the ventricular assist device drive console 1 is equipped with a switch that serves to interlock the ventricular assist device 2 and the balloon 4 without simultaneous driving thereof, and select switch that settles the ratio of the driving frequency of the ventricular assist device 2 per beat of the patient's heart (duty ratio). Blood is removed from he left atrium and pumped into the aorta by the ventricular assist device 2. When the failed heart has gained recovery by the aid of the ventricular assist device 2 and the weaning is initiated, the balloon 4 is inserted via the femoral artery while the ventricular assist device 2 is attached o the patient's body. Subsequently, a duty ratio of 8/8 for the ventricular assist device drive console 1 and the combination use drive mode is selected. When a duty ratio of 8/8 as been selected, only the ventricular assist device 2 is driven. When a duty ratio of 7/8 has been selected, the ventricular assist device 2 and the balloon 4 are driven at rates of 7 beats and 1 beat, respectively, per 8 beats of the patient's heart. When a duty ratio of 6/8 has been selected, the ventricular assist device 2 and the balloon 4 account for 3 beats and 1 beat, respectively, per 8 beats of the patient's heart. By varying the duty ratio according to the degree of recovery of the failed heart and increasing the ratio of the driving frequency of the balloon 4, it is possible to smoothly shift from the ventricular assist device 2 to the balloon 4.

Figure 2:
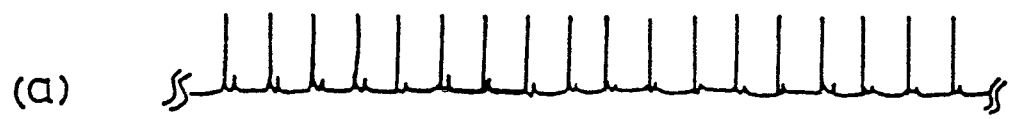
FIG. 2 shows the allotments of pulsations to the ventricular assist device and the balloon in a mode of embodiment of the present invention.
Figure 2:
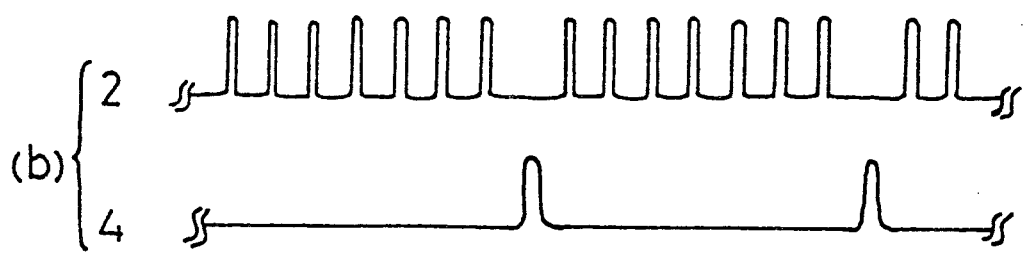
Figure 2:
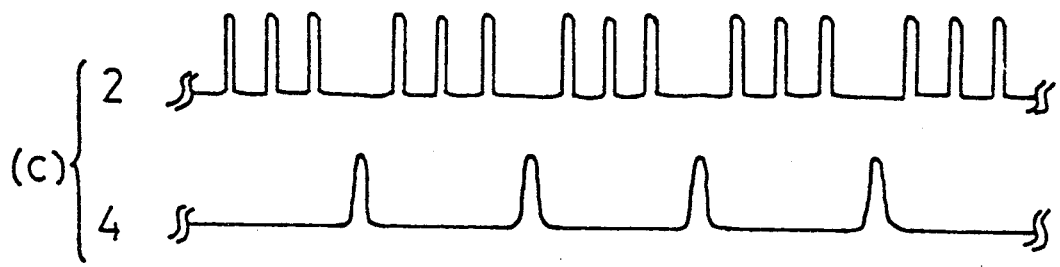
Figure 2:
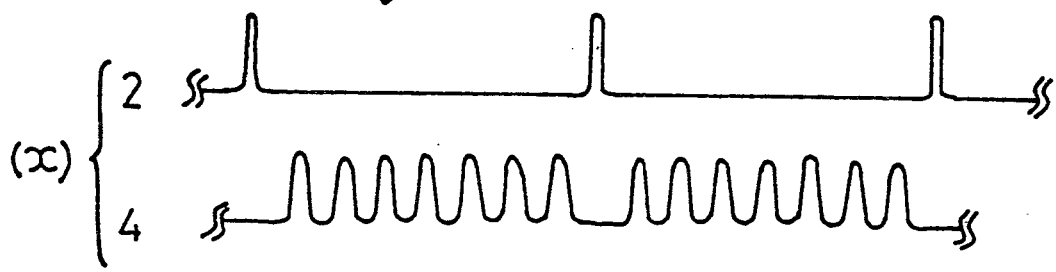

It is also possible to automatically alter the duty ratio so that the left atrial pressure and the total blood flow (total of the patient's cardiac output flow and output flow from the ventricular assist device 2) can be maintained constant. In FIG. 2, a beat pattern of the patient's heart and the timing charts of the ventricular assist device 2 and the balloon 4 are shown.

In FIG. 2, Panel (a) shows an electrocardiogram of the patient's heart; Panels (b), (c) and (x) show driving timing charts of the ventricular assist device 2 and the balloon 4 in accordance with the present invention, taken at a duty ratio of 7/8 for the initial weaning stage for Panel (b), at a duty ratio of 6/8 for Panel (c), and at a duty ratio of 1/8 for the last weaning stage for Panel (x).

Figure 3A:
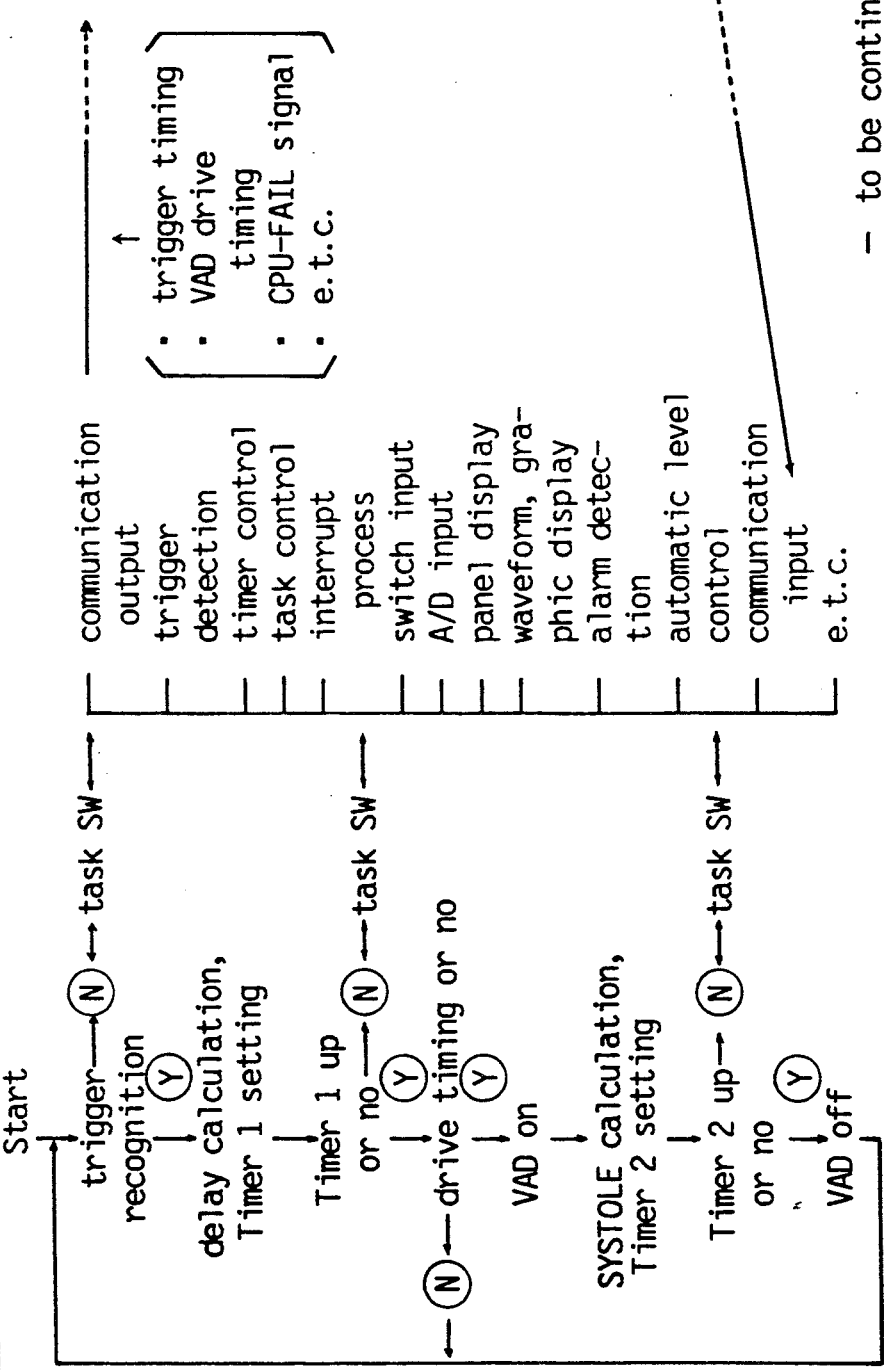
FIGS. 3a and 3b are a flow chart schematizing the action of the microcomputer in a mode of embodiment of the present invention.
Figure 3:
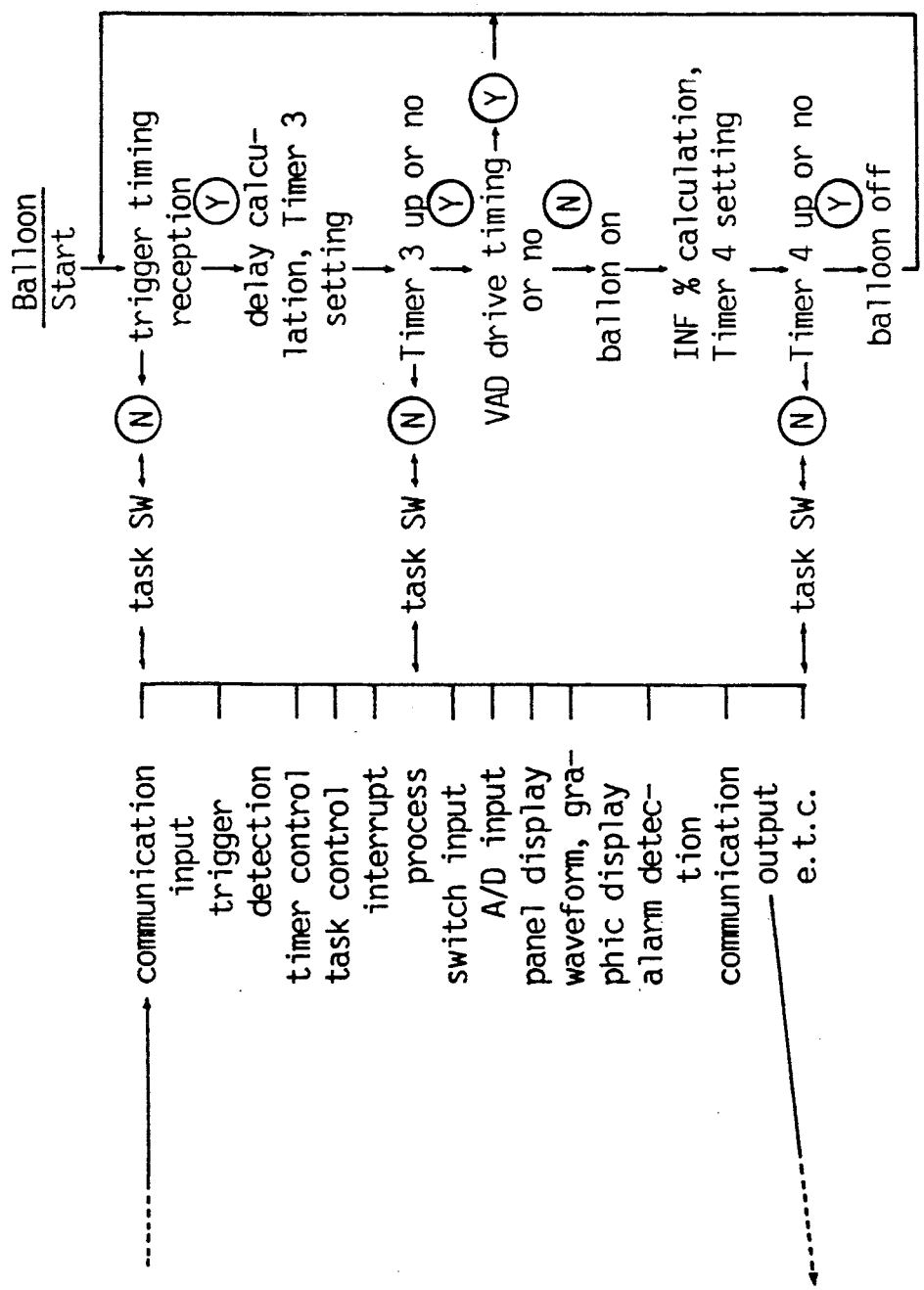

FIGS. 3a and 3b are a flow chart schematizing the action of the microcomputer.

The ventricular assist device drive console and the balloon drive console read the mode digital switch and recognize the interlocking (combination use) mode.

The ventricular assist device drive console recognizes waveforms to detect trigger points, while processing other tasks (e.g. switching detection, graphic display, alarm detection). After trigger point detection, it sends a trigger timing signal and a ventricular assist device driving allowance signal to the balloon drive console.

Subsequently, time lag for driving the ventricular assist device is calculated and Timer 1 is set. Until Timer 1 time setting is reached, other tasks are processed concurrently. When Timer 1 time setting is reached, the ventricular assist device driving allowance signal is confirmed, and if it is not detected, operation of the ventricular assist device drive console returns to the starting point. If the signal is detected, the positive pressure valve of the ventricular assist device is opened (negative pressure valve closed), and opening time is calculated and Timer 2 is set. Until Timer 2 time setting is reached, other tasks are processed concurrently.

When Timer 2 time setting is reached, the positive pressure valve of the ventricular assist device is closed (negative pressure valve opened) and operation of the ventricular assist device drive console returns to the starting point.

Upon trigger timing signal reception, the balloon drive calculates time lag for balloon driving and Timer 3 is set. Until Timer 3 time setting is reached, other tasks are processed concurrently. When Timer 3 time setting is reached, the balloon drive confirms the ventricular assist device driving allowance signal sent from the ventricular assist device drive console, and if the signal is detected, operation of the balloon returns to the starting point. If it is not detected, the positive pressure valve of the balloon is opened (negative pressure valve closed), opening time is calculated and Timer 4 is set. Until Timer 4 time setting is reached, other tasks are processed concurrently. When Timer 4 time setting is reached, the positive pressure valve of the balloon is closed (negative valve opened) and operation of the balloon returns to the starting point.

As stated above, the ventricular assist device operates at a given duty ratio, and the balloon is driven instead during the ventricular assist device causes. Thus, the duty ratio of the balloon changes with alteration of the duty ratio of the ventricular assist device drive console, which facilitates weaning with simple operation.

Use of the apparatus of the present invention and method of its driving permits weaning from the driving or wearing of the ventricular assist device with simple operation without extreme reduction in the output per beat of the ventricular assist device or severely influencing the patient's body upon recovery of the failed heart.

We claim:

1. An assist circulation apparatus for facilitating weaning from a ventricular assist device when a failed heart of a patient has nearly gained recovery, the assist circulation apparatus comprising, in combination:
    a left ventricular assist device for supplementing the pumping function of the failed heart;
    an intra-aortic balloon catheter device for weaning from the left ventricular assist device;
    means for controlling the driving frequencies of both the left ventricular assist device and the balloon catheter device to prevent simultaneous driving thereof; and
    means for arbitrarily altering the ratio of the driving frequencies of the left ventricular assist device and the balloon catheter device in order to increase the balloon catheter driving frequency in relation to the left ventricular assist device driving frequency, so that weaning of the patient from the left ventricular assist device is facilitated.

2. The apparatus as set forth in claim 1 wherein the means for arbitrarily altering comprises selection means for selecting and altering the ratio of the driving frequencies of the left ventricular assist device and the balloon catheter device.

3. The apparatus as set forth in claim 1 wherein the means for controlling comprises switch means for interlocking the driving of the left ventricular assist device and the balloon catheter device and preventing simultaneous driving thereof.

4. In a system for supplementing the pump function of a failed heart in a patient which utilizes a ventricular assist device in combination with an intra-aortic balloon catheter device for weaning from the ventricular assist device, an assist circulating apparatus comprising:

ventricular assist drive means for controlling the ventricular assist device;

balloon catheter drive means for controlling the balloon catheter device;

means for preventing simultaneous driving of the ventricular assist device and the balloon catheter device; and means for arbitrarily altering the ratio of the driving frequencies of the two devices in order to increase the balloon catheter driving frequency in relation to the ventricular assist device driving frequency so that weaning of the patient from the ventricular assist device is facilitated.

5. The apparatus as set forth in claim 4 wherein the means for preventing comprises switch means for interlocking the driving of the ventricular assist device and the balloon catheter device and preventing simultaneous driving thereof.

6. The apparatus as set forth in claim 4 wherein the means for arbitrarily altering comprises selection means for selecting and altering the ratio of the driving frequencies of the ventricular assist device and the balloon catheter device.

7. The apparatus as set forth in claim 4 further comprising:

communication means for interconnecting the ventricular assist drive means and the balloon catheter drive means.

8. A method of driving an assist circulation apparatus which utilizes a ventricular assist device in combination with an intra-aortic balloon catheter device for weaning from the ventricular assist device, the method comprising:

providing driving frequencies to the ventricular assist device and the balloon catheter device;

controlling the driving frequencies of both the ventricular assist device ad the balloon catheter device to prevent simultaneous driving thereof; and arbitrarily altering the ratio of the driving frequencies of the ventricular assist device and the balloon catheter device in order to increase the balloon catheter driving frequency in relation to the ventricular assist device driving frequency, so that weaning of the patient from the ventricular assist device is facilitated.

* * * * *

UNITED STATES PATENT AND TRADEMARK OFFICE
CERTIFICATE OF CORRECTION

PATENT NO. : 5,129,878

DATED : July 14, 1992

INVENTOR(S) : Takano et al.

It is certified that error appears in the above-identified patent and that said Letters Patent is hereby corrected as shown below:

Column 1, line 49, delete "he" and substitute therefor -- the --;

Column 3, line 9, delete "he" and substitute therefor -- the --;

Column 3, line 14, delete "o" and substitute therefor -- to --;

Column 4, line 24, delete "causes" and substitute therefor -- pauses --;

Claim 4, column 4, line 68, delete "circulating" and substitute therefor -- circulation --;

Claim 8, column 6, line 14, delete "ad" and substitute therefor -- and --.

Signed and Sealed this

Twenty-eighth Day of September, 1993

Attest:

BRUCE LEHMAN

*Attesting Officer*     *Commissioner of Patents and Trademarks*